(12) United States Patent
Shuros et al.

(10) Patent No.: US 9,517,017 B2
(45) Date of Patent: Dec. 13, 2016

(54) RECONSTRUCTION OF CARDIAC ACTIVATION INFORMATION BASED ON ELECTRICAL AND MECHANICAL MEANS

(71) Applicant: Boston Scientific Scimed, Inc., Maple Grove, MN (US)

(72) Inventors: Allan C. Shuros, St. Paul, MN (US); Pramodsingh H. Thakur, Woodbury, MN (US); Sunipa Saha, Shoreview, MN (US); Barun Maskara, Blaine, MN (US); Shibaji Shome, Arden Hills, MN (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 247 days.

(21) Appl. No.: 14/154,972

(22) Filed: Jan. 14, 2014

(65) Prior Publication Data

US 2014/0200457 A1    Jul. 17, 2014

Related U.S. Application Data

(60) Provisional application No. 61/752,241, filed on Jan. 14, 2013.

(51) Int. Cl.
*A61B 5/02* (2006.01)
*A61B 8/12* (2006.01)
(Continued)

(52) U.S. Cl.
CPC ............... *A61B 5/02* (2013.01); *A61B 5/0422* (2013.01); *A61B 5/1107* (2013.01); *A61B 8/12* (2013.01);
(Continued)

(58) Field of Classification Search
CPC combination set(s) only.
See application file for complete search history.

(56) References Cited

U.S. PATENT DOCUMENTS 5,582,609 A    12/1996    Swanson et al.
5,588,432 A    12/1996    Crowley
(Continued)

FOREIGN PATENT DOCUMENTS

CN    101156774 A    4/2008
CN    102421356 A    4/2012
(Continued)

OTHER PUBLICATIONS

Gurev et al., "Distribution of Electromechanical Delay in the Heart: Insights from a Three-Dimensional Electromechanical Model", Biophysics Journal, vol. 99, Aug. 2010, pp. 745-754.*
(Continued)

*Primary Examiner* — Katherine Fernandez
*Assistant Examiner* — Farshad Negarestan
(74) *Attorney, Agent, or Firm* — Faegre Baker Daniels LLP

(57) ABSTRACT

An anatomical mapping system includes a plurality of mapping electrodes, a plurality of mechanical sensors, and a mapping processor associated with the plurality of mapping electrodes and mechanical sensors. The mapping electrodes are configured to detect electrical activation signals of intrinsic physiological activity within an anatomical structure. The mechanical sensors are configured to detect mechanical activity associated with the intrinsic physiological activity. The mapping processor is configured to record the detected activation signals and associate one of the plurality of mapping electrodes and mechanical sensors with each recorded activation signal. The mapping processor is further configured to determine activation times of the
(Continued)

intrinsic physiological activity based on a correlation of corresponding electrical activation signals and mechanical activity.

16 Claims, 3 Drawing Sheets

(51) Int. Cl.
*A61B 5/042* (2006.01)
*A61B 5/11* (2006.01)
*A61B 5/00* (2006.01)
*A61B 5/0452* (2006.01)
*A61B 18/00* (2006.01)
*A61B 18/14* (2006.01)

(52) U.S. Cl.
CPC ............ *A61B 5/0452* (2013.01); *A61B 5/6858* (2013.01); *A61B 18/1492* (2013.01); *A61B 2018/00357* (2013.01); *A61B 2018/00577* (2013.01); *A61B 2090/064* (2016.02); *A61B 2562/0204* (2013.01); *A61B 2562/0219* (2013.01)

(56) References Cited

U.S. PATENT DOCUMENTS

| | | | |
|---|---|---|---|
| 5,647,870 A | 7/1997 | Kordis et al. | |
| 5,840,031 A | 11/1998 | Crowley | |
| 5,954,649 A | 9/1999 | Chia et al. | |
| 6,004,269 A | 12/1999 | Crowley et al. | |
| 6,029,671 A | 2/2000 | Stevens et al. | |
| 6,070,094 A | 5/2000 | Swanson et al. | |
| 6,233,477 B1* | 5/2001 | Chia | A61B 5/0422 600/424 |
| 6,233,491 B1 | 5/2001 | Kordis et al. | |
| 6,246,899 B1 | 6/2001 | Chia et al. | |
| 6,259,941 B1 | 7/2001 | Chia et al. | |
| 6,296,630 B1 | 10/2001 | Altman et al. | |
| 6,735,465 B2 | 5/2004 | Panescu | |
| 7,029,466 B2 | 4/2006 | Altman | |
| 7,517,315 B2 | 4/2009 | Willis | |
| 7,547,301 B2 | 6/2009 | Altman et al. | |
| 7,610,078 B2 | 10/2009 | Willis | |
| 7,655,005 B2 | 2/2010 | Bhola | |
| 2001/0044619 A1 | 11/2001 | Altman | |
| 2002/0019623 A1 | 2/2002 | Altman et al. | |
| 2003/0032998 A1 | 2/2003 | Altman | |
| 2005/0080469 A1 | 4/2005 | Larson et al. | |
| 2005/0149008 A1 | 7/2005 | Larson et al. | |
| 2005/0165298 A1 | 7/2005 | Larson et al. | |
| 2005/0165388 A1 | 7/2005 | Bhola | |
| 2005/0171527 A1 | 8/2005 | Bhola | |
| 2006/0058775 A1 | 3/2006 | Stevens et al. | |
| 2006/0094956 A1 | 5/2006 | Viswanathan | |
| 2007/0049821 A1 | 3/2007 | Willis | |
| 2007/0049826 A1 | 3/2007 | Willis | |
| 2007/0135803 A1 | 6/2007 | Belson | |
| 2008/0015542 A1 | 1/2008 | Altman et al. | |
| 2008/0086073 A1 | 4/2008 | McDaniel | |
| 2009/0306732 A1 | 12/2009 | Rosenberg et al. | |
| 2010/0268059 A1 | 10/2010 | Ryu et al. | |
| 2011/0092809 A1 | 4/2011 | Nguyen et al. | |
| 2014/0121470 A1* | 5/2014 | Scharf | A61B 5/0422 600/301 |

FOREIGN PATENT DOCUMENTS

| | | |
|---|---|---|
| JP | 2007524466 A | 8/2007 |
| JP | 2008534165 A | 8/2008 |
| JP | 2009536560 A | 10/2009 |
| WO | WO9724981 A2 | 7/1997 |
| WO | WO2010131178 A1 | 11/2010 |

OTHER PUBLICATIONS

International Search Report and Written Opinion issued in PCT/US2014/011481, mailed Apr. 29, 2014, 16 pgs.

Ryu et al., Simultaneous Electrical and Mechanical Mapping Using 3D Cardiac Mapping System: Novel Approach for Optimal Cardiac Resynchronization Therapy, Journal of Cardiovascular Electrophysiology, vol. 21, No. 2, Feb. 1, 2010, 4 pgs.

International Preliminary Report on Patentability issued in PCT/US2014/011481, mailed Jul. 23, 2015, 12 pages.

* cited by examiner

RECONSTRUCTION OF CARDIAC ACTIVATION INFORMATION BASED ON ELECTRICAL AND MECHANICAL MEANS

CROSS-REFERENCE TO RELATED APPLICATIONS

This application claims the benefit under 35 U.S.C. section 119(e) to U.S. provisional application No. 61/752,241 entitled "RECONSTRUCTION OF CARDIAC ACTIVATION INFORMATION BASED ON ELECTRICAL AND MECHANICAL MEANS", filed on Jan. 14, 2013, which is herein incorporated by reference in its entirety.

TECHNICAL FIELD

The present disclosure relates to anatomical mapping. More particularly, the present disclosure relates correlating electrical activation signals and mechanical activity associated with an intrinsic physiological activity detected by electrical and mechanical means for mapping an anatomical structure.

BACKGROUND

Physicians make use of catheters in medical procedures to gain access into interior regions of the body for diagnostic and therapeutic purposes. It is important for the physician to be able to precisely position the catheter within the body to gain contact with a desired tissue location. During these procedures, a physician steers the catheter through a main vein or artery into the interior region of the heart that is to be treated. The physician then further manipulates a steering mechanism to place the electrode carried on the distal tip of the catheter into direct contact with the endocardial tissue. The physician directs energy from the electrode through myocardial tissue either to an indifferent electrode (in a unipolar electrode arrangement) or to an adjacent electrode (in a bi-polar electrode arrangement) to ablate the tissue.

Before ablating heart tissue, physicians often examine the propagation of electrical impulses in heart tissue to locate aberrant conductive pathways and to identify the arrhythmia foci, which are ablated. The techniques used to analyze these pathways and locate foci are commonly called mapping.

SUMMARY

In Example 1, an anatomical mapping system includes a plurality of mapping electrodes, a plurality of mechanical sensors, and a mapping processor associated with the plurality of mapping electrodes and mechanical sensors. The plurality of mapping electrodes is configured to detect electrical activation signals of intrinsic physiological activity within an anatomical structure. The plurality of mechanical sensors is configured to detect mechanical activity associated with the intrinsic physiological activity. The mapping processor is configured to record the detected activation signals and associate one of the plurality of mapping electrodes and mechanical sensors with each recorded activation signal. The mapping processor is further configured to determine activation times of the intrinsic physiological activity based on a correlation of corresponding electrical activation signals and mechanical activity.

In Example 2, the anatomical mapping system according to Example 1, wherein the mapping processor is further configured to generate an activation map based on the determined activation times and transmits the generated activation map to a display unit.

In Example 3, the anatomical mapping system according to either Example 1 or Example 2, and further including a reference mechanical sensor disposed outside of the anatomical structure and not influenced by the mechanical activity in the anatomical structure, the reference sensor configured to receive motion data associated with the mechanical activity from the mechanical sensors.

In Example 4, the anatomical mapping system according to any of Examples 1-3, wherein the mechanical sensors and reference mechanical sensor are piezoelectric crystals.

In Example 5, the anatomical mapping system according to any of Examples 1-4, wherein the mechanical sensors are configured to transmit ultrasonic signals related to the mechanical activity and the reference mechanical sensor is configured to receive the ultrasonic signals.

In Example 6, the anatomical mapping system according to any of Examples 1-5, wherein the mapping processor is further configured to generate a reliability index for each determined activation time according to the correlation, the reliability index based on the detection of an activation signal by a mapping electrode and a mechanical sensor in close proximity to the detecting mapping electrode.

In Example 7, the anatomical mapping system according to any of Examples 1-6, wherein the mapping processor is further configured to determine the presence of at least one pathology at a mapping electrode location and/or mechanical sensor location based on the reliability index.

In Example 8, an anatomical mapping system includes a plurality of mapping electrodes, a plurality of mechanical sensors, and a mapping processor associated with the plurality of mapping electrodes and mechanical sensors. The plurality of mapping electrodes is configured to detect electrical activation signals of cardiac activity, each of the plurality of mapping electrodes having an electrode location. The plurality of mechanical sensors is configured to detect mechanical activity associated with the cardiac activity, each of the plurality of mechanical sensors having a mechanical sensor location. The mapping processor is configured to record the detected activation signals from the mapping electrodes and motion data associated with the mechanical activity and correlate the detected activation signals with the mechanical activity. The mapping processor is further configured to identify a pathology at each electrode location based on whether only electrical activity, only mechanical activity, or both electrical and mechanical activity are detected at each electrode location and mechanical sensor location.

In Example 9, the anatomical mapping system according to Example 8, wherein the mapping processor is further configured to determine activation times of the cardiac activity based on the correlation of the detected activation signals with the mechanical activity.

In Example 10, the anatomical mapping system according to either Example 8 or Example 9, wherein the mapping processor is further configured to generate an activation map based on the determined activation times.

In Example 11, the anatomical mapping system according to any of Examples 8-10, and further including a reference mechanical sensor disposed outside of the anatomical structure and not influenced by the mechanical activity, the reference sensor configured to receive motion data associated with the mechanical activity from the mechanical sensors.

In Example 12, the anatomical mapping system according to any of Examples 8-11, wherein the mechanical sensors and reference mechanical sensor are piezoelectric crystals.

In Example 13, the anatomical mapping system according to any of Examples 8-12, wherein the mechanical sensors are configured to transmit ultrasonic signals related to the mechanical activity and the reference mechanical sensor is configured to receive the ultrasonic signals.

In Example 14, the anatomical mapping system according to any of Examples 8-13, wherein the mapping processor is further configured to generate a reliability index for each determined activation time according to the correlation, the reliability index based on the detection of an activation signal by a mapping electrode and a mechanical sensor in close proximity to the detecting mapping electrode.

In Example 15, the anatomical mapping system according to any of Examples 8-14, wherein the mapping processor is further configured to determine the presence of an arrhythmic rotor according to a determined reliability index.

In Example 16, the anatomical mapping system according to any of Examples 8-15, wherein the mapping processor is further configured to determine a location of the arrhythmic rotor and output the location to a display unit.

In Example 17, a method for mapping an anatomical structure includes detecting electrical activation signals of intrinsic physiological activity within the anatomical structure, detecting mechanical activity associated with the intrinsic physiological activity with a mapping catheter, correlating the detected activation signals with the mechanical activity, and determining activation times of the intrinsic physiological activity based on a correlation of corresponding electrical activation signals and mechanical activity.

In Example 18, the method according to Example 17, further including identifying a pathology based on whether only electrical activity is detected, only mechanical activity is detected, or both electrical and mechanical activity are detected.

In Example 19, the method according to either Example 17 or Example 18, further including displaying a location of the pathology on a map of the anatomical structure.

In Example 20, the method according to any of Examples 17-19, further including generating an activation map based on the activation times; and displaying the activation map.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
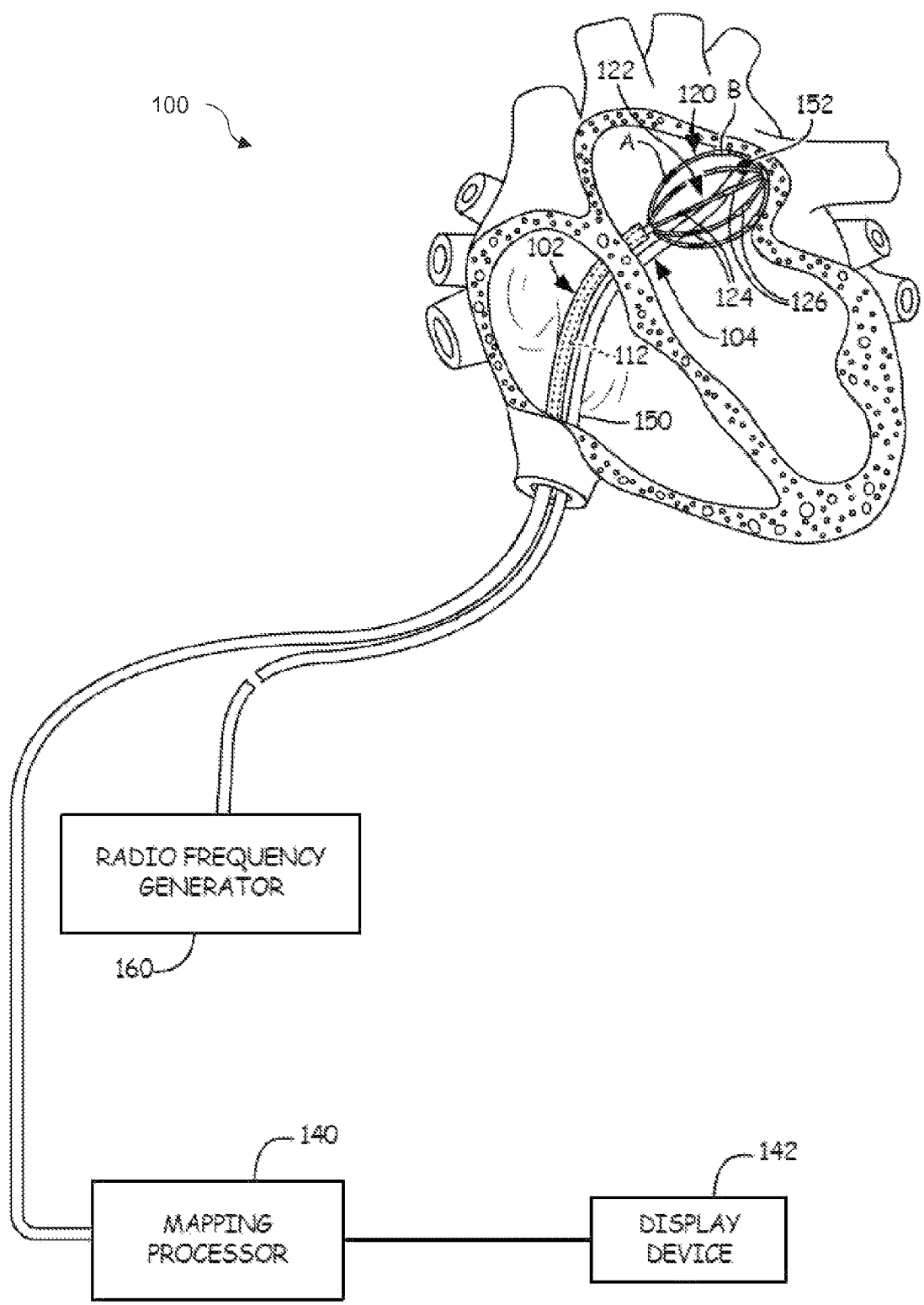
FIG. 1 is a schematic view of an embodiment of a cardiac activation reconstruction system for mapping an anatomical region in the body.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

Although the term "block" may be used herein to connote different elements of illustrative methods employed, the term should not be interpreted as implying any requirement of, or particular order among or between, various steps disclosed herein unless and except when explicitly referring to the order of individual steps.

DETAILED DESCRIPTION

FIG. 1 illustrates an embodiment of a cardiac activation reconstruction system 100 for accessing a targeted tissue region in the body for diagnostic or therapeutic purposes. FIG. 1 generally shows the system 100 deployed in the left atrium of the heart. Alternatively, the system 100 can be deployed in other regions of the heart, such as the right atrium, left ventricle, or right ventricle. While the illustrated embodiment shows the system 100 being used for ablating heart tissue, the system 100 (and the methods described herein) may alternatively be configured for use in other tissue ablation applications, such as procedures for ablating tissue in the prostrate, brain, gall bladder, uterus, and other regions of the body, including in systems that are not necessarily catheter-based.

The system 100 includes a mapping probe 102 and an ablation probe 104. In FIG. 1, each is separately introduced into a selected heart region 110 through a vein or artery (e.g., the femoral vein or artery, inferior vena cava, or the like) through suitable percutaneous access. Alternatively, the mapping probe 102 and the ablation probe 104 can be assembled in an integrated structure for simultaneous introduction and deployment in the heart region 110.

The mapping probe 102 has a flexible body 112. A distal end of the probe body 112 carries a three-dimensional sensing structure 120. In the illustrated embodiment, the sensing structure 120 takes the form of a basket defining an open interior space 122 (see FIG. 2); although other types of structures could be used. The sensing structure 120 carries a plurality of mapping electrodes 124 configured to detect electrical activation signals of intrinsic physiological activity within the anatomical structure on which the ablation procedure is to be performed. For example, the mapping electrodes 124 can be configured to detect electrical activation signals of an intrinsic cardiac activity within a heart. The sensing structure 120 further carries a plurality of mechanical sensors 126 configured to detect mechanical activity associated with the intrinsic physiological activity. For example, the mechanical sensors 126 can be configured to detect or measure motion data intrinsic to the cardiac activity of the heart such as myocardial contraction. The mapping electrodes 124 and the mechanical sensors 126 can be referred to collectively as sensors 124 and 126.

The sensors 124 and 126 are electrically coupled to a mapping processor 140. A signal wire (not shown) is electrically coupled to each mapping electrode 124 and to each mechanical sensor 126 on the sensing structure 120. The wires extend through the probe body 112 of the mapping probe 102 and electrically couples each of the sensors 124, 126 to the mapping processor 140. The sensed electrical and mechanical activity is processed by the mapping processor 140 to assist the physician in identifying the site or sites within the heart appropriate for ablation.

In some embodiments, the mapping processor 140 is configured to record the detected activation signals (including electric signals and mechanical signals) and associate one of the plurality of mapping electrodes 124 and mechanical sensors 126 with each recorded signal. For example, the mapping processor 140 may record an electrical activation signal originating from a mapping electrode A and a mechanical activation signal originating from a mechanical sensor B. The mapping processor 140 can be configured to associate the detected signals to sensors A and B. The mapping processor 140 is further configured to determine activation times of the intrinsic physiological activity based on correlation of corresponding electrical activation signals and mechanical activity as will be described further below.

In some embodiments, the mapping processor 140 may be configured to measure the intrinsic electrical activity and the mechanical activity associated with the intrinsic electrical activity in the heart tissue adjacent to the mapping electrodes 124 and the mechanical sensors 126 respectively. For example, in some embodiments, the mapping processor 140 is configured to detect intrinsic electrical activity and the corresponding mechanical activity associated with a dominant rotor in the anatomical structure being mapped. Studies have shown that dominant rotors have a role in the initiation and maintenance of atrial fibrillation, and ablation of the rotor path and/or rotor core may be effective in terminating the atrial fibrillation. In some embodiments, the mapping processor 140 processes the sensed information to derive the location of a site appropriate for ablation using the ablation probe 104.

The ablation probe 104 includes a flexible probe body 150 that carries one or more ablation electrodes 152. The one or more ablation electrodes 152 are electrically connected to a radio frequency generator 160 that is configured to deliver ablation energy to the one or more ablation electrodes 152. The ablation probe 104 is movable with respect to the anatomical structure to be treated, as well as the sensing structure 120. The ablation probe 104 is positionable between or adjacent to the sensors 124, 126 of the sensing structure 120 as the one or more ablation electrodes 152 are positioned with respect to the tissue to be treated.

In the illustrated embodiment, the mapping processor 140 includes an output display device 142 (e.g., a CRT, LED display, or a printer). The display device 142 presents a graphical representation of the intrinsic physiological activity, e.g., electrical and/or mechanical activation signals, to the physician which may be useful for remotely guiding the ablation electrode 152 within the basket structure 120.

Figure 2:
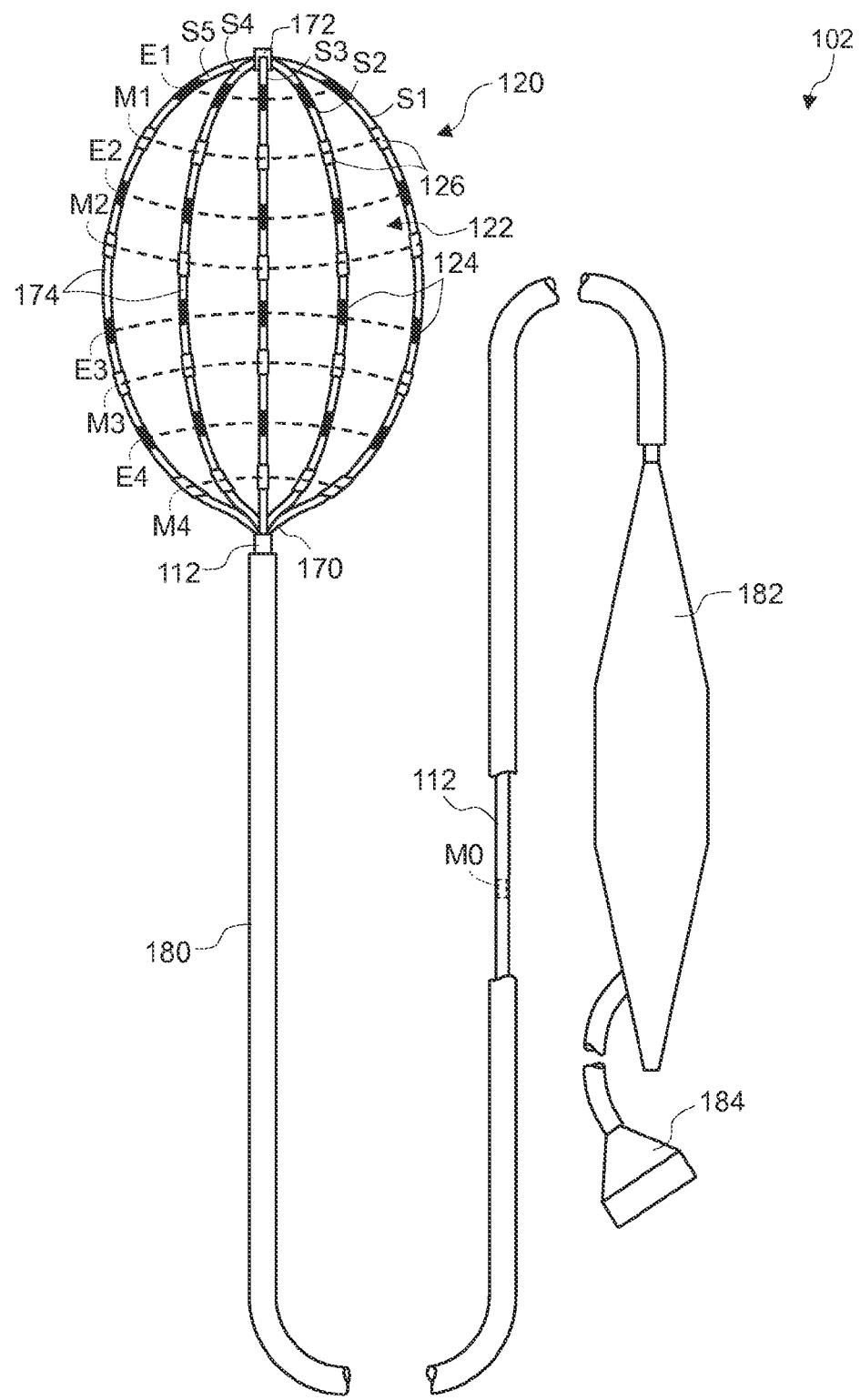
FIG. 2 is a side view of an embodiment of a mapping catheter having a basket functional element carrying structure including a plurality of mapping electrodes and a plurality of mechanical sensors for use in association with the system of FIG. 1.

FIG. 2 illustrates an embodiment of the mapping probe 102 including the mapping electrodes 124 and the mechanical sensors 126 at the distal end, suitable for use in the system 100 shown in FIG. 1. The mapping probe 102 has the probe body 112, the distal end of which carries the sensing structure 120 configured to carry the mapping electrodes 124 and the mechanical sensors 126. The mapping electrodes 124 sense intrinsic electrical activity in the heart tissue while the mechanical sensors 126 sense mechanical activity such as, for example, myocardial contraction. The sensed electrical and mechanical activity is then processed by the mapping processor 140 to assist the physician in identifying a site or sites having a pathology, e.g. a heart rhythm disorder. This process is commonly referred to as mapping. This information can then be used to determine an appropriate location for applying appropriate therapy, e.g. ablation therapy, to the identified sites, and to navigate the one or more ablation electrodes 152 to the identified sites.

The illustrated sensing structure 120 includes a base member 170 and an end cap 172, between which flexible splines 174 generally extend in a circumferentially spaced relationship. As discussed above, the sensing structure 120 takes the form of a basket defining the open interior space 122. In some embodiments, the splines 174 are made of a resilient inert material, such as, e.g., Nitinol metal or silicone rubber, and are connected between the base member 170 and the end cap 172 in a resilient, pretensed condition to bend and conform to the tissue surface they contact. In the illustrated embodiment, five splines 174 (labeled S1, S2, S3, S4, and S5) are shown to form the sensing structure 120. Additional or fewer splines could be used in other embodiments. For example, in one example alternative embodiment, the sensing structure 120 includes eight splines. As illustrated, each spline 174 carries four mapping electrodes 124 (labeled E1, E2, E3, and E4) and four mechanical sensors 126 (labeled M1, M2, M3, and M4). Additional or fewer mapping electrodes 124 and mechanical sensors 126 could be disposed on each spline 174 in other embodiments of the sensing structure 120. For example, in one example alternative embodiment, each spline 174 carries eight mapping electrodes 124. In the illustrated embodiment, the sensing structure 120 is relatively small (e.g., 40 mm or less in diameter). In alternative embodiments, the sensing structure 120 is larger (e.g., 40 mm in diameter or greater).

The mapping probe 102 also includes a reference mechanical sensor M0 disposed a distance away from the mapping electrodes 124 and the mechanical sensors 126. For example, the reference mechanical sensor M0 can be disposed on the probe body 112 and outside of an anatomical structure to be mapped, e.g. 10 to 20 cm away. The reference mechanical sensor M0 is thus generally not influenced by the mechanical activity in the anatomical structure.

In some embodiments, the reference mechanical sensor M0 and the mechanical sensors 126 (M1, M2, M3, and M4) are piezoelectric sensors or crystals. The piezoelectric crystals are both actuators and receivers which generate and emit ultrasound signals (at a frequency range of 100 kHz to at least several MHz) that are then received by the other piezoelectric crystals 126 and M0. Distances, and changes in distances between the mechanical sensors 126, M0 can then be calculated based on the time necessary for the ultrasound signals to propagate through the tissue and blood. The speed of sounds through the tissue/blood medium can be assumed to be constant. In this way, movement of the mechanical sensors 126, M0 due to physiological activity such as myocardial contraction can be determined. Additionally, when an electrical potential is applied to the mechanical sensors 126, an ultrasonic mechanical signal is generated. The mechanical sensors 126 transmit ultrasonic signals which are deflected by intrinsic physiological activity, e.g. cardiac activity. The deflected ultrasonic signals are received by the reference mechanical sensor M0. For example, the mechanical sensors 126 can be electrically excited, causing them to emit ultrasound signals in the form of motion data. The reference mechanical sensor M0 receives the emitted ultrasonic signals, i.e. motion data, and measures a recognition time of the ultrasonic signals from each mechanical sensor 126. Upon mechanical deformation of the adjacent anatomical structure, the sensing structure 120, upon which the mechanical sensor(s) 126 are disposed, is deformed and thus the emitted ultrasonic signal is deflected causing a detectable variation in the recognition time of the ultrasonic signal, i.e., motion data, to the reference mechanical sensor M0.

The ultrasonic signals from the plurality of mechanical sensors can be differentiated from one another by varying the frequency of individual mechanical sensors. Alternatively, the reference mechanical sensor M0 can generate an ultrasonic reference signal which is received by the mechanical sensors 124 at various recognition times according to their location relative to M0. Upon receipt of the reference signal, each mechanical sensor generates an electrical response with is recorded by the mapping processor 140. The mapping processor can identify activation signals based on a timestamp of the electrical signal generated by each mapping electrode 124. The reference mechanical sensor M0 and the mechanical sensors 126 can be used in a bi-polar configuration for the measure of motion data associated with the mechanical activity. Alternatively, the reference mechanical sensor M0 and the mechanical sensors 126 can be used in a uni-polar or multi-polar configuration for the measure of motion data associated with the mechanical activity.

A slidable sheath 180 is movable along the major axis of the probe body 112. Moving the sheath 180 forward (i.e., toward the distal end) causes the sheath 180 to move over the sensing structure 120, thereby collapsing the sensing structure 120 into a compact, low profile condition suitable for introduction into the interior space 122, such as, for example, into the heart. In contrast, moving the sheath 180 rearward (i.e., toward the proximal end) frees the sensing structure 120, allowing the sensing structure 120 to spring open and assume the pretensed position illustrated in FIG. 2. Further details of embodiments of the sensing structure 120 are disclosed in U.S. Pat. No. 5,647,870 entitled "Multiple Electrode Support Structures," which is hereby incorporated by reference in its entirety.

A signal wire (not shown) is electrically coupled to each sensor 124, 126, M0. The wires extend through the probe body 112 of the mapping probe 102 into a handle 182, in which they are coupled to an external connector 184, which may be a multiple pin connector. The connector 184 electrically couples the sensors 124, 126, M0 to the mapping processor 140. Further details on mapping systems and methods for processing signal generated by the mapping probe are discussed in U.S. Pat. No. 6,070,094, entitled "Systems and Methods for Guiding Movable Electrode Elements within Multiple-Electrode Structure," U.S. Pat. No. 6,233,491, entitled "Cardiac Mapping and Ablation Systems," and U.S. Pat. No. 6,735,465, entitled "Systems and Processes for Refining a Registered Map of a Body Cavity," the disclosures of which are incorporated herein by reference.

Although mapping sensors have been described as being carried by dedicated probes, such as the mapping probe 102, the sensors such as the mapping electrodes 124 and the mechanical sensors 126 can be carried on non-mapping dedicated probes or catheters. For example, an ablation catheter, such as the ablation probe 104, can be configured to include one or more mapping sensors and/or mechanical sensors disposed on the distal end of the catheter body and coupled to the mapping processor 140. As another example, the ablation electrode 152 at the distal end of the ablation probe 104 may be coupled to the mapping processor 140 to also operate as a mapping sensor.

After the sensing structure 120 is positioned adjacent to the anatomical structure to be treated, the mapping processor 140 receives signals from the mapping electrodes 124, the mechanical sensors 126, and the reference mechanical sensor M0 related to intrinsic physiological activity of the anatomical structure. A detected electrical signal is indicative of local depolarization of the anatomical location that would result in myocardial contraction locally at the anatomical location. Generally, therefore, the electrical signal detected by a mapping electrode such as the mapping electrode E2 is followed or associated (occurring simultaneously or substantially simultaneously) with a local mechanical activity of the tissue detected by a mechanical sensor such as the mechanical sensor M2 in proximity of the mapping electrode E2, both in close proximity of the anatomical location from which the electrical and mechanical activity originate from. The mapping processor 140 can be configured to receive electrical signals from the mapping electrode E2, the mechanical sensor M2, and the reference mechanical sensor M0 that are indicative of the electrical activity (depolarization) and the corresponding mechanical activity that is the myocardial contraction as a result of the depolarization. In some embodiments, mechanical assessment of the cardiac activity based on the detected signal from a mechanical sensor M0 may involve assessment of active contraction and resultant deformation of the local myocardium relative to other areas of the mapped region. In some embodiments, radial and circumferential strain may be assessed from the mechanical sensors 126 alone for detection of the mechanical activity. In some embodiments, frequency of the spline deformation associated with a mechanical sensor compared to deformation from other splines corresponding to other mechanical sensors may be used as a basis for assessment of mechanical activity. Upon receipt of signals indicative of the electrical and mechanical activity, the mapping processor 140 is configured to associate the signals with the location of the respective sensors, i.e. mapping electrodes 124 and mechanical sensors 126.

In some embodiments, the mapping processor 140 is configured to correlate the activation times recorded by the mapping electrodes 124 with the corresponding mechanical activity detected by the mechanical sensors 126 and/or the reference mechanical sensor M0 according to a timestamp associated with the activation signal. The activation signals detected as electrical signals by the mapping electrodes are assigned a timestamp and the activation signals detected as mechanical activity by the mechanical sensors 126 are also assigned a timestamp. The mapping processor 140 correlates the corresponding electrical and mechanical activation signals according to temporal and/or spatial proximity, i.e., an electrical activation signal occurs at or near the same time as a mechanical activation signal and/or electrical activation signal occurs at or near the same location as a mechanical activation signal, respectively. The correlation identifies detected activation signals whether they are electrical or mechanical in nature. An electro-mechanical delay can then be calculated based on the correlation. A map of electro-mechanical delay values can then be generated to visualize the anatomical regions associated with electromechanical delays.

The mapping processor 140 is also configured to generate an activation map based on recorded electrical and/or mechanical activation signals and their corresponding electro-mechanical delay to generate at least one of an electrical activation map, mechanical activation map, an electro-mechanical activation map, and an electro-mechanical delay map. The activation map can be displayed on the display device 142 for analysis by a physician. For example, the physician can study activation map to identify regions of pathology suitable for therapy, e.g. ablation therapy.

The mapping processor 140 is also configured to generate a reliability index for each correlated activation signal. The reliability index can be based on whether only electrical activity, only mechanical activity, both electrical and mechanical activities are recorded for each identified activation signal, or the corresponding electro-mechanical delay. The reliability indices can be used to determine if a suspected pathology site is suitable for therapy. For example, if mechanical and electrical activity is detected at an identified pathology site, this may be indicative of a myocardial contraction after depolarization of the anatomical structure, and thus would indicate the occurrence of a local activation. This local activation may indicate that the adjacent tissue is active though dysfunctional and would be a good candidate for therapy, e.g. ablation therapy of a dominant rotor. In contrast, if only an electrical activity is detected, this may be an indication of an absence of local myocardial contraction after depolarization. However, since the tissue is still electrically active and thus live tissue, it may still be a good candidate for therapy, such as ablation of the pathology site. In some correlated activation signals, mechanical activity may be detected without any presence or detection of electrical activity. This may be an indication of contraction of myocardial tissue without local depolarization. A physician or an operator may, in such cases, identify the contraction as originating from a source other than the local depolarization. This may possibly occur because of some other reasons such as, for example, far field activity and may not require therapy of the local anatomical structure due to the necrotic local tissue.

In some embodiments, the reliability index may be defined on the basis of the spatial proximity of the mechanical sensor relative to the mapping electrode, in addition to the correlation. For example, the mechanical sensor may be proximate the corresponding mapping electrode at the anatomical structure or, alternatively, the mechanical sensor may be positioned far (not proximate) to the mapping electrode at the anatomical structure. A close proximity of the mechanical sensor may confirm that the source of the mechanical activation, e.g. myocardial contraction, corresponds to the depolarization of the anatomical location detected by the proximately located electrode. Otherwise, a lack of proximity may bear a substantial probability that the mechanical activation signal corresponds to a depolarization that occurs from a far field event. The mechanical activation may thus not further confirm the electrical activation with a high reliability.

The mapping processor 140 can be configured to determine the location of an arrhythmic rotor and output the location to the display unit. In some embodiments, each determined activation onset time can be associated with a reliability index. The generated activation maps and, for example, the rotor location can accordingly be based on and associated with the reliability index. In some embodiments, the mapping processor 140 determined a pathology location, such as the location of a rotor, if a certain level of reliability, as identified from the reliability index, is established. The mapping processor 140 can be configured to identify if a pathology is present at each electrode location based on such as whether only electrical activity, only mechanical activity, or both electrical and mechanical activity are detected at each electrode location and mechanical sensor location.

To treat the pathology, the ablation electrode 152 of the ablation probe 104 is moved relative to the sensing structure 120 until the ablation electrode 152 is positioned adjacent to or against the anatomical structure where a dominant rotor or other pathology to be treated is detected proximate to the basket structure 120. The ablation electrode 152 may pass through the interior space 122 of the sensing structure 120 to reach the anatomical structure to be treated, for example.

In various embodiments, various types of ablation probes can be used such as for ablating the mapped locations identified as rotors or with other pathology. Exemplary configurations employing multiple ablation electrodes are possible as described in U.S. Pat. No. 5,582,609, entitled "Systems and Methods for Forming Large Lesions in Body Tissue Using Curvilinear Electrode Elements," which is hereby incorporated by reference in its entirety. Various other conventionally available ablation catheters may be used in conjunction with the present disclosure or multiple ablation electrodes can be integrated within the mapping catheter to integrate the ablation functionality within the mapping catheter.

The system described herein performs sufficient assessment of intrinsic physiological activity for locating pathology, e.g., arrhythmic rotor path and/or core, or other pathology. The system can identify heterogeneities within the tissue in a targeted area of the anatomical structure that may not be perceivable by using electrical means alone. In addition, the mechanical assessment of the intrinsic physiological activity performed by the system for locating a pathology may be less susceptible to noise as compared to the electrical assessments alone. Furthermore, the mechanical assessment performed by the system may be able to detect areas of tissue exhibiting high degrees of stretch and/or strain which maybe more aberrant, to detect areas of thicker, more complex tissue structures, and may be able to detect strain patterns in the tissue. Therefore, the system can be more sensitive to localizing a pathology, such as an arrhythmic rotor path and/or core positions, for therapy thereof.

Figure 3:
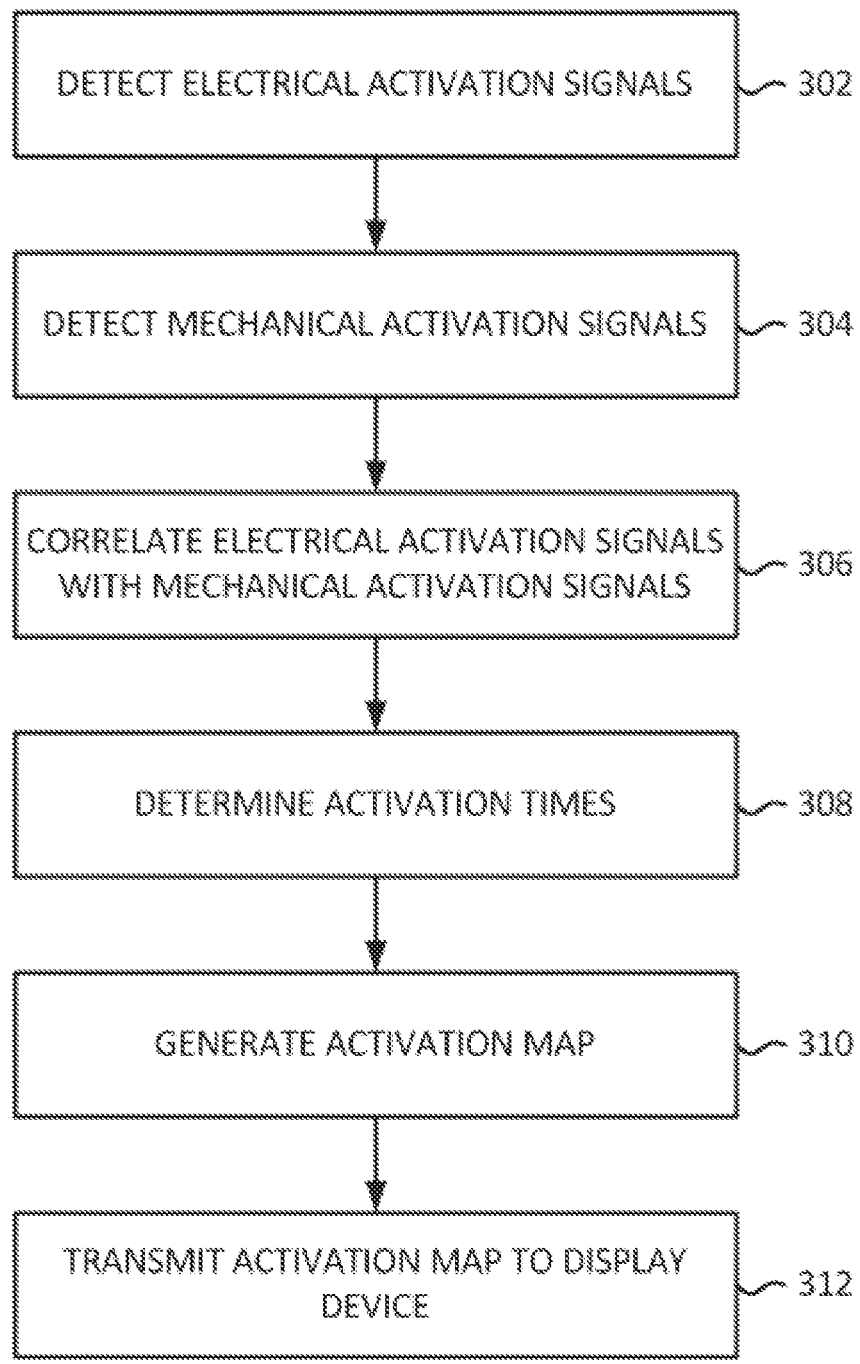
FIG. 3 is a flow diagram depicting a method for mapping an anatomical structure in accordance with embodiments of the invention.

Thus, as depicted in FIG. 3, a method for mapping an anatomical structure, such as heart, to be treated for an arrhythmic disorder using the system described herein includes detecting electrical activation signals of intrinsic physiological activity within the anatomical structure (block 302). Mapping electrodes 124 disposed on a basket structure 120 can be deployed in the heart and used for detecting electrical activation signals. The electrical activation signals can be electrical pulses generated due to electrical depolarization of a portion of the cardiac region to be mapped.

Mechanical activation signals, resulting from mechanical activity, associated with the intrinsic physiological activity are detected concurrently with the electrical activation signals (block 304). Mechanical sensors 126 disposed on the basket structure 120 in concert with a reference mechanical sensor M0 are used for detecting the mechanical activity. In some embodiments, the mechanical sensors 126 and reference sensor M0 can be piezoelectric crystals. The mechanical activity can be motion data generated due to myocardial contraction of an anatomical location of the heart.

The method further includes correlating the detected electrical activation signals with the mechanical activation signals, i.e. mechanical activity (block 306). The mapping processor 140 can be used for correlating the detected electrical activation signals with the mechanical activity. The mapping processor 140 records the electrical activation signal and the mechanical activity and associates the mechanical activity and the electrical signal with the mapping electrodes 124 and the mechanical sensors 126 respectively. The mapping processor 140 then correlates the recorded electrical activation signals with the mechanical activity for a specific mapping electrode location and a mechanical sensor location, i.e., the anatomical location to be mapped.

The activation times of the intrinsic physiological activity are determined based on the correlation of the corresponding electrical activation signals and the mechanical activity (block 308). The mapping processor 140 can identify local activation times and determine onset times from information obtained from an electrical signal detected by the mapping electrode 124 at the anatomical location. Similarly, the mapping processor 140 can identify local activation times and determine onset times from information obtained from a mechanical activity detected by the mechanical sensor 126 disposed at the anatomical location. The mapping processor 140 can then correlate the activation times obtained from the mechanical activity and the activation times obtained from the electrical activity to obtain correlated activation time for the physiological activity at the anatomical location.

An activation map can be generated based on the determined and/or correlated activation times (block 310) and transmitted to a display device 142 (block 312) for review by a physician to identify and location pathologies in the cardiac tissue such as arrhythmic disorders, e.g. a dominant rotor, rotor core, or rotor path. In some embodiments, the method can include identifying an anomaly or pathology at the anatomical location. The pathology can be identified based on whether only the electrical activity, only the mechanical activity or both are detected. The detection of the pathology can be associated with a reliability index also based on such as whether only the electrical activity, only the mechanical activity or both are detected. The location of the pathology can be displayed on the activation map of the anatomical structure.

When the location of the pathology is identified, a target location suitable for therapy can be determined. A therapy device, such as an ablation catheter, is positioned adjacent to the targeted location and therapeutic energy is applied to treat the pathology.

The mapping processor 140 can be configured to generate a delay map for assessment of the delay between the electrical activation signal and the mechanical activation signal at a corresponding location and all locations of the anatomical structure. A map of the electro-mechanical delay can be used during sinus or paced rhythms to identified regions suffering from a pathology such as an arrhythmic disorder.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An anatomical mapping system comprising:
a plurality of mapping electrodes configured to detect electrical activation signals of intrinsic physiological activity within an anatomical structure and to generate electrical signals indicative of the detected electrical activation signals;
a plurality of mechanical sensors configured to detect local mechanical activity associated with the intrinsic physiological activity and to generate electrical signals indicative of the detected local mechanical activity, wherein each of the plurality of mechanical sensors is further configured to transmit ultrasound signals;
a reference mechanical sensor disposed outside of the anatomical structure, the reference sensor configured to receive the transmitted ultrasound signals from the plurality of mechanical sensors and to generate, in response to receiving the transmitted ultrasound signals, an electrical signal indicative of movement, due to the intrinsic physiological activity, of at least one mechanical sensor of the plurality of mechanical sensors; and
a mapping processor associated with the plurality of mapping electrodes, mechanical sensors, and the reference mechanical sensor, the mapping processor configured to (1) receive and record the electrical signals indicative of the detected electrical activation signals, the electrical signals indicative of the detected local mechanical activity, and the electrical signals indicative of the movement of the at least one mechanical sensor; (2) associate one of the plurality of mapping electrodes and one of the plurality of mechanical sensors with each recorded electrical signal; and (3) determine activation times of the intrinsic physiological activity based on a correlation of corresponding detected electrical activation signals and mechanical activity, the mechanical activity comprising the movement, due to the physiological activity, of the at least one mechanical sensor.

2. The anatomical mapping system according to claim 1, wherein the mapping processor is further configured to generate an activation map based on the determined activation times and transmits the generated activation map to a display unit.

3. The anatomical mapping system according to claim 1, further comprising a probe body and a sensing structure disposed at a distal end of the probe body, wherein the reference mechanical sensor is disposed on the probe body, and wherein the plurality of mapping electrodes and the plurality of mechanical sensors are disposed on the sensing structure.

4. The anatomical mapping system according to claim 1, wherein the mechanical sensors and the reference mechanical sensor are piezoelectric crystals.

5. The anatomical mapping system according to claim 1, wherein the transmitted ultrasonic signals comprise data related to the mechanical activity.

6. The anatomical mapping system according to claim 1, wherein the mapping processor is further configured to generate a reliability index for each determined activation time according to the correlation, wherein the reliability index is based on the detection of an electrical activation signal by a mapping electrode and the detection of local mechanical activity by a mechanical sensor in close proximity to the detecting mapping electrode.

7. The anatomical mapping system according to claim 6, wherein the mapping processor is further configured to determine a presence of at least one pathology at a mapping electrode location and/or mechanical sensor location based on the reliability index.

8. An anatomical mapping system comprising:
a plurality of mapping electrodes configured to detect electrical activation signals of cardiac activity within a cardiac structure and to generate electrical signals indicative of the detected electrical activation signals, each of the plurality of mapping electrodes having an electrode location;
a plurality of mechanical sensors configured to detect local mechanical activity associated with the cardiac activity, and to generate electrical signals indicative of the detected mechanical activity, each of the plurality of mechanical sensors having a mechanical sensor location, wherein each of the plurality of mechanical sensors is further configured to transmit ultrasound signals;

a reference mechanical sensor disposed outside of the cardiac structure, the reference sensor configured to receive the transmitted ultrasound signals from the plurality of mechanical sensors and to generate, in response to receiving the transmitted ultrasound signals, an electrical signal indicative of movement, due to the cardiac activity, of at least one mechanical sensor of the plurality of mechanical sensors; and a mapping processor associated with the plurality of mapping electrodes, the plurality of mechanical sensors, and the reference mechanical sensor, the mapping processor configured to: (1) receive and record the electrical signals indicative of the detected electrical activation signals, the electrical signals indicative of the detected mechanical activity, and the electrical signal indicative of the movement of the at least one mechanical sensor; (2) determine activation times of the cardiac activity by correlating the detected electrical activation signals with the detected local mechanical activity and the movement, due to cardiac activity, of the at least one mechanical sensor; and (3) identify a pathology based on whether only electrical activity, only mechanical activity, or both electrical activity and mechanical activity are detected at each mapping electrode location and each mechanical sensor location, respectively, the mechanical activity comprising the movement, due to cardiac activity, of the at least one mechanical sensor;

wherein the mapping processor is further configured to generate, for each determined activation time, a reliability index, wherein each reliability index is based on the detection of an electrical activation signal by a mapping electrode and the detection of local mechanical activity by a mechanical sensor in close proximity to the detecting mapping electrode.

9. The anatomical mapping system according to claim 8, wherein the mapping processor is further configured to generate an activation map based on the determined activation times.

10. The anatomical mapping system according to claim 8, wherein the mechanical sensors and reference mechanical sensor are piezoelectric crystals.

11. The anatomical mapping system according to claim 8, wherein the mapping processor is further configured to determine a presence of an arrhythmic rotor according to a determined reliability index.

12. The anatomical mapping system according to claim 11, wherein the mapping processor is further configured to determine a location of the arrhythmic rotor and output the location to a display unit.

13. A method for mapping an anatomical structure, the method comprising:

detecting electrical activation signals of intrinsic physiological activity within the anatomical structure with a mapping catheter, the mapping catheter comprising a plurality of mapping electrodes;

generating, by the plurality of mapping electrodes, electrical signals indicative of the detected electrical activation signals;

detecting, using a plurality of mechanical sensors, local mechanical activity associated with the intrinsic physiological activity;

generating, by the plurality of mechanical sensors, electrical signals indicative of the detected local mechanical activity;

transmitting, by each of the plurality of mechanical sensors, ultrasound signals;

receiving, using a reference mechanical sensor disposed outside of the anatomical structure, the transmitted ultrasound signals from the mechanical sensors;

generating, by the reference mechanical sensor and in response to receiving the transmitted ultrasound signals, an electrical signal indicative of movement, due to the intrinsic physiological activity, of at least one mechanical sensor of the plurality of mechanical sensors;

receiving and recording, by a mapping processor associated with the plurality of mapping electrodes and mechanical sensors, the electrical signals indicative of the detected electrical activation signals, the electrical signals indicative of the detected local mechanical activity, and the electrical signals indicative of the movement of the at least one mechanical sensor;

associating, by the mapping processor, one of the plurality of mapping electrodes and one of the plurality of mechanical sensors with each recorded electrical signal;

correlating, by the mapping processor, the detected electrical activation signals with mechanical activity comprising the local mechanical activity and the movement, due to the physiological activity, of the at least one mechanical sensor;

determining, by the mapping processor, activation times of the intrinsic physiological activity based on the correlation of corresponding electrical activation signals and the mechanical activity; and generating, for each determined activation time, a reliability index, wherein each reliability index is based on the detection of an electrical activation signal by a mapping electrode and the detection of local mechanical activity by a mechanical sensor in close proximity to the detecting mapping electrode.

14. The method of claim 13, and further comprising:

identifying a pathology based on whether only electrical activity is detected, only mechanical activity is detected, or both electrical and mechanical activity are detected at each mapping electrode location and each mechanical sensor location.

15. The method of claim 13, and further comprising:

determining an electromechanical delay from the detected electrical activation signals and the mechanical activity; and generating an electromechanical delay map based on the determined electromechanical delay.

16. The method of claim 13, and further comprising:

generating an activation map based on the determined activation times; and displaying the activation map.

* * * * *